US 7,633,616 B2

(12) United States Patent
Hing

(10) Patent No.: US 7,633,616 B2
(45) Date of Patent: Dec. 15, 2009

(54) APPARATUS AND METHOD FOR PHOTO-ELECTRIC MEASUREMENT

(75) Inventor: Paul Anthony Hing, Owingen (DE)

(73) Assignee: Sensovation AG, Stockach (DE)

( * ) Notice: Subject to any disclaimer, the term of this patent is extended or adjusted under 35 U.S.C. 154(b) by 116 days.

(21) Appl. No.: 10/559,140

(22) PCT Filed: Jun. 2, 2003

(86) PCT No.: PCT/EP03/05758

§ 371 (c)(1),
(2), (4) Date: Sep. 21, 2006

(87) PCT Pub. No.: WO2004/106874

PCT Pub. Date: Dec. 9, 2004

(65) Prior Publication Data

US 2007/0057159 A1    Mar. 15, 2007

(51) Int. Cl.
*G01J 3/26* (2006.01)
(52) U.S. Cl. .................................... 356/326
(58) Field of Classification Search ................ 356/326, 356/328, 300–301
See application file for complete search history.

(56) References Cited

U.S. PATENT DOCUMENTS

| 5,074,157 | A | | 12/1991 | Marsoner et al. |
| 5,159,199 | A | | 10/1992 | LaBaw |
| 5,420,681 | A | * | 5/1995 | Woodruff ................. 356/326 |
| 5,623,340 | A | * | 4/1997 | Yamamoto et al. ........ 356/237.4 |
| 5,724,437 | A | | 3/1998 | Bucher et al. |
| 5,993,634 | A | | 11/1999 | Simpson et al. |
| 6,791,680 | B1 | * | 9/2004 | Rosengaus et al. ........ 356/237.2 |
| 2004/0202577 | A1 | * | 10/2004 | McNeil et al. ........... 422/82.08 |
| 2004/0239773 | A1 | * | 12/2004 | Bleau et al. ............. 348/211.99 |

FOREIGN PATENT DOCUMENTS

| DE | 43 21 177 A1 | 1/1995 |
| DE | 296 18 918 U1 | 2/1997 |
| DE | 102 14 517 A1 | 6/2003 |
| EP | 0 918 434 A2 | 5/1998 |
| EP | 1 037 458 A1 | 9/2000 |

(Continued)

OTHER PUBLICATIONS

International Search Report—PCT/EP 03/05758.

*Primary Examiner*—Kara E Geisel
(74) *Attorney, Agent, or Firm*—Husch Blackwell Sanders Welsh & Katz

(57) ABSTRACT

An apparatus and a method for photo-electric measurement is included; the apparatus comprises photo-electric conversion devices and an optical system which is modularly expandable in order to acquire electromagnetic radiation from a line or area of any desired size on an object. The optical system preferably separates the electromagnetic radiation modularly into a plurality of smaller segments and projects electromagnetic radiation corresponding to the smaller segments onto individual photo-electric conversion devices and sensor electronics related to said photo-electric conversion device(s). This enables the operating mode and functionality of said photo-electric conversion device(s) to be defined and changed in real-time, whereby functions such as the readout sequence of pixels and unlimited flexibility of pixel binning in two dimensions are fully programmable, and the photo-electric conversion device(s) can operate and/or be controlled independently and/or simultaneously.

52 Claims, 7 Drawing Sheets

FOREIGN PATENT DOCUMENTS

| | | |
|---|---|---|
| FR | 2 784 794 A1 | 4/2000 |
| WO | WO 90/02326 | 3/1990 |
| WO | WO 95/21378 | 8/1995 |
| WO | WO 98/53301 | 11/1998 |
| WO | WO 99/35506 | 7/1999 |
| WO | WO 00/11024 | 3/2000 |
| WO | WO 02/25934 A2 | 3/2002 |
| WO | WO 2004/106874 A1 | 12/2004 |

* cited by examiner

APPARATUS AND METHOD FOR PHOTO-ELECTRIC MEASUREMENT

BACKGROUND OF THE INVENTION

Optical imaging combined with spectroscopy is commonly used for the analysis and testing of substances and materials, such as chemicals, molecules, cells, tissue, and the like, and for measurement/detection of related reactions, processes and events. These substances or processes may be arranged in units, hereto referred to collectively as "samples", in order to facilitate handling and analysis. In order to increase speed, throughput, efficiency and to decrease cost, increasingly large numbers of samples are analyzed simultaneously in parallel, or alternatively in a high-speed serialized fashion, or a combination thereof. In many applications, a plurality of samples to be measured are prepared and organized such that they can be analyzed in an automated fashion, whereby they are placed in or on a "sample carrier", typically in the format of an array. The sample carrier facilitates the handling, transport and processing of samples. In addition to the measurement of samples, it is increasingly important that information related to the samples and their related carriers, packaging, etc. be acquired ("read" or "measured"), as well as created, tracked, and managed in general. Such "sample information" may exist in various forms, including stored on computers, databases, lists, files, stored on integrated circuits, barcodes, or encoded onto the samples themselves. Furthermore, the said sample information may be directly readable and/or modifiable from the object to be measured, for example from sample carriers and/or from the samples themselves.

Currently the most common examples of applications from the biotechnology field include the use of microscopic analysis on microscope slides; sample analysis on microplates which can hold commonly 96, 384, or 1536 samples, multi-channel electrophoresis, multi-capillary electrophoresis, and cell-based analysis via cytometry. One strategy to increase throughput while still conforming to the microplate format is to place the samples in an "array of arrays", whereby an increased number of samples are placed where a single sample used to be. This preserves the investment in automation systems which handle microplates. Recent advances in miniaturization include "biological chips (biochips)" and "micro-arrays" which accommodate up to hundreds of thousands of samples, whereby the physical size and volume of the samples approach the micron and sub-nanoliter ranges respectively. Further modern methods involve molecular-based sample analysis or processing on miniaturized solid substrates such as on micro-beads. The number of samples on one sample carrier is currently approaching a few million. Typically the biochemical process is monitored or a result is detected by optical measurement, primarily using fluorescence spectroscopy, chemi-luminescence, and optical absorbance and/or reflectance, whereby each and every of the mentioned samples must be analyzed. The prevalent detection method in the biotechnology field utilizes fluorescence, whereby one or more fluorescent labels are used to identify, discriminate and/or analyze the samples.

Current measurement and detection technology in this field are based on:

a) Imaging, typically using cooled scientific CCD and CID cameras. Such array sensors have the inherent advantage of parallelism—that is, they allow the simultaneous measurement of a plurality of samples arranged on a plane surface. Spectral measurement is implemented by using interchangeable optical filters. The samples are typically illuminated or excited either simultaneously, or by scanning a light source over the area.

b) Scanning systems, typically involving the scanning of a laser over the sample carrier area, with measurement using one or more optical sensors such as Photomultiplier Tubes (PMT) or Avalanche Photodiodes. Spectral measurement is implemented either by using a number (n) of interchangeable optical filters with a single sensor, implying that the area to be measured must be scanned (n) times; or a plurality of sensors, each used with an optical filter. "Confocal" optical schemes, which limit the focal plane of measurement have been used with scanning systems to increase sensitivity, and to allow a third dimension of measurement in the "Z" or focal axis.

c) Scanning confocal systems which make use of an image sensor such as a CCD (Charge Coupled Device) are known. For example, WO 95/21378 discloses a scanning single-beam confocal apparatus for DNA sequencing, using a CCD-based spectrometer. WO 00/11024 is another such example where multiple laser beam excitation is employed with confocal multiple-spectra detection by a CCD sensor. Current instrumentation have limitations on the size of the area that can be measured, the resolution that can be achieved, and the speed of measurement. Furthermore, the performance and/or consistency of measurements vary with sample position over the area to be measured. Sensitivity decreases as the area (number of samples, throughput and speed) increases.

Imaging systems based on cameras commonly are employing increasingly larger image sensors, with as small pixels as possible. This has disadvantages of lower device yields and higher cost; slower readout rates due to the larger number of pixels; optical aberrations in standard imaging optics are increasingly problematic; and the inevitable resolution limit of semiconductor technology. To perform spectroscopy, multiple images using various optical filters are acquired, leading to longer measurement time, and lower sensitivity. Laser scanning systems also suffer from the same optical imaging problems caused by aberrations as the area as well as the resolution increases. Demands increase on the precision of the mechanically scanning mirror, and reliability and robustness are issues at the relatively high scanning speeds. Sensitivity decreases due to the increased time multiplexing inherent in scanning, as well as the use of optical filters. The flatness and tilt of the surface or volume to be measured, as well as its positioning relative to the sensing system poses a problem as the area gets larger. The resulting variation in focus within the measurement area leads to location-dependent performance.

SUMMARY

The object of the present invention is to provide an apparatus and methods for optical imaging and spectral measurement of areas and volumes, which solve one or several of the above problems.

The advantages of this invention over prior art are:

Measurement of large areas: The size of the two dimensional area to be measured is theoretically unlimited. On one axis, the optical measurement unit is modularly expandable to the desired length without affecting the speed of measurement. Along other axis, either the optical measurement unit moves relative to the area to be measured for any desired length, or the micro-optical sensor may be similarly extended in this dimension also.

According to the present invention many smaller CCD devices are used in parallel instead of one large device. For example, as opposed to imaging an entire Microplate onto one large, expensive CCD, many smaller fields (perhaps each well) can be imaged at lower resolution. Smaller devices have less pixels—i.e., lower capacitances—and are inherently capable of running faster. Through the parallel readout of many devices, overall throughput is greatly increased—even if the readout rate is reduced in order to decrease noise. Smaller devices have higher production yields, and as mentioned above, less expensive optics can be used. By designing the parallelism modularly, the throughput can be indefinitely increased without speed penalty. In comparison to large devices, there is a limit to increasing the resolution, as the cost of the device increases. Speed (frame rate) decreases as the device gets larger. Since the areas to be imaged are very small and are typically spaced apart (e.g. in the 96-well plate), it is more efficient to use micro-optical arrays. In effect an array of objective lenses.

Better light collection efficiency: Replacing single, larger optical components with smaller size ("micro-") optics or arrays thereof enables the achievement of high numerical aperture and high system etendue. Furthermore, this performance can be extended such that it is consistent over an arbitrarily large area. By decreasing the field of view and resolution requirements for each sensor, the demands on its corresponding optics are lower. It is also easier to design more efficient, fast excitation and emission optics. This enables the use of micro- or mini-optics.

It is preferable to use CHARGE MULTIPLYING CCD (hereafter CM-CCD) devices (frame transfer type of CCD), which can detect single-electrons at high speeds. This is achieved by multiplying the charge packets on-chip, before they are read at the CCD output. Granted that at high readout and frame rates the read noise of the output is relatively high, one detected electron is multiplied with a gain high enough to produce a signal much greater than the read noise. This newer technology allows novel and radically different approaches in comparison to using deep-cooled CCD cameras with extremely low noise together with long integration times.

Enables confocal optical system: By replacing a single imaging optics essentially with one or more smaller optical system(s), each of the latter is able to function as an individual confocal system. The inherent advantages of confocal systems include lower background signal and the capability to perform 3-dimensional imaging of volumes. This invention furthermore enables the implementation of an "adaptive" confocal system which can adapt to unevenness and tilt of the area or volume to be measured.

Low background signal: In the case of fluorescence spectroscopy where high sensitivity is required, "background" signal often sets the limit of detection. This background largely originates from undesired light such as fluorescence (e.g. from the sample carrier, reagents which may contain the samples, or from other samples which are not being measured), and from scattered or stray light. This invention reduces background by illuminating (exciting) as well as collecting light only from the point to be measured. Furthermore, by implementing a confocal system background is further eliminated by confining the light collection to a defined focal plane.

This invention further decreases background via "gated fluorescence spectroscopy", whereby fluorescence is collected during its decay lifetime when the illumination (excitation) is off.

Ability to optimize spectral bands: Programmability of the width of spectral bands to be measured allows optimizing of sensitivity vs. spectral resolution. In the limit, the highest sensitivity is achieved when the entire spectrum is summed together into a single measurement. This can be done via charge binning on the sensor, which minimizes noise.

High speed: A plurality of relatively small spectrographic array sensors operate in parallel at high speeds. The number of such sensors with associated miniaturized optics can be modularly increased indefinitely to accommodate large measurement areas without compromising speed. As opposed to using one large, slow array sensor, this modular use of an array of smaller sensors is faster particularly as the measurement area increases.

Consistent performance over the area/volume to be measured:

The efficiency of illumination (excitation) and light collection of the scanning optical measurement system is consistent over the entire area to be measured. This provides higher reliability and quality of data from samples. The modular optical system, and/or scanning along an axis replaces a single standard imaging system, eliminating common location-dependent problems such as those caused by vignetting and optical aberrations.

Spectral imaging with high spectral resolution or programmable spectral bands: The compact, miniaturized optical system integrates optional diffractive elements, which together with the array sensor allows a digitized spectrum to be measured. This is more efficient than using optical filters, and is faster since all wavelengths are simultaneously acquired. Furthermore, the apparatus allows full programmability of the readout of the array sensor, so that the spatial location of samples as well as the spectral bands to be measured can be changed, optimized and/or calibrated in real time.

Ability to perform measurements in many modes, and/or to operate in a plurality of modes simultaneously: This can be useful for performing real-time optimization such as auto-focus or sample location (via imaging) while performing spectroscopic measurements.

Spectroscopic measurement of a plurality of discrete detection points (samples) widely spaced within a relatively large area. There may be large "dead spaces" between the detection points. This is useful for example when analyzing samples in microplates, or lab-on-chip applications where samples may be analyzed via electrophoresis in micro-fluidic channels. In the latter, detection points may be as small as tens of microns and spaced many millimeters or centimeters apart.

Lower Cost

Allows the use of standard size array sensors. Using a plurality of available smaller sensors is a more cost-effective solution since the volumes for the devices increases, production yield for small devices with less pixels is higher. The preferred use of micro-optics, which may be in the form of inexpensive replicated parts replaces expensive high performance imaging optics.

High Reliability and Robustness

Integrated miniaturized optical systems are inherently more mechanically stable, less susceptible to dust and dirt. A fully solid-state system eliminates vacuum tubes (for example photomultiplier tubes), mechanical filter wheels. Real-time adaptivity allows tolerances, for example in mechanical positioning, spectral drift.

"Sample-Based Detection":

This invention allows the apparatus to be programmed, controlled and optimised by the user on a "sample basis"—to think and to optimise the system in terms of the application's goal for each and every individual sample to be measured—i.e., achieving best and most reliable sample analysis results. Furthermore, the said optimisation occurs in real-time closed-loop fashion. This is a systems-based approach, in which the invention goes beyond generating images and delivering pixel values. For example, in spectroscopy applications, the system can be programmed to optimise the spectral binning vs. sensitivity on an individual sample-by-sample basis.

Compact, light detection unit suitable for mounting on moving robotic axes. The space required for the sensing unit in an optical system is minimal.

The present invention can be used in a number of target markets including, but not limited to:

Biotechnology Instrumentation

Pharmaceutical (Drug discovery, High Throughput Screening)

Clinical lab automation

Medical Diagnostics, Medical Instruments, Telemedicine

Agriculture

Animal husbandry

Environmental Monitoring and Controls

Law enforcement, Human Identification, Forensics

The invention is especially suitable for meeting the demands of high-throughput applications in which a plurality of miniaturized samples to be measured are located over a very large area or volume. Such applications include spectroscopy; microscopy; biochemical assays; processes and reactions on miniaturized formats (such as those involving micro-/nano-plates, micro-formats & micro-arrays, chemistry-on-chip, lab-on-chip, micro-channels and micro-fluidics, where dimensions of the samples are on micron scale and volumes are in the sub-nanoliter range). Typical "sample carriers" which hold a plurality of samples are microplates, gel plates, microscope slides, or a plurality thereof.

BRIEF DESCRIPTION OF THE DRAWINGS

The invention is now described with reference to the preferred embodiments and the drawings, in which.

DETAILED DESCRIPTION

Figures 1, 2:
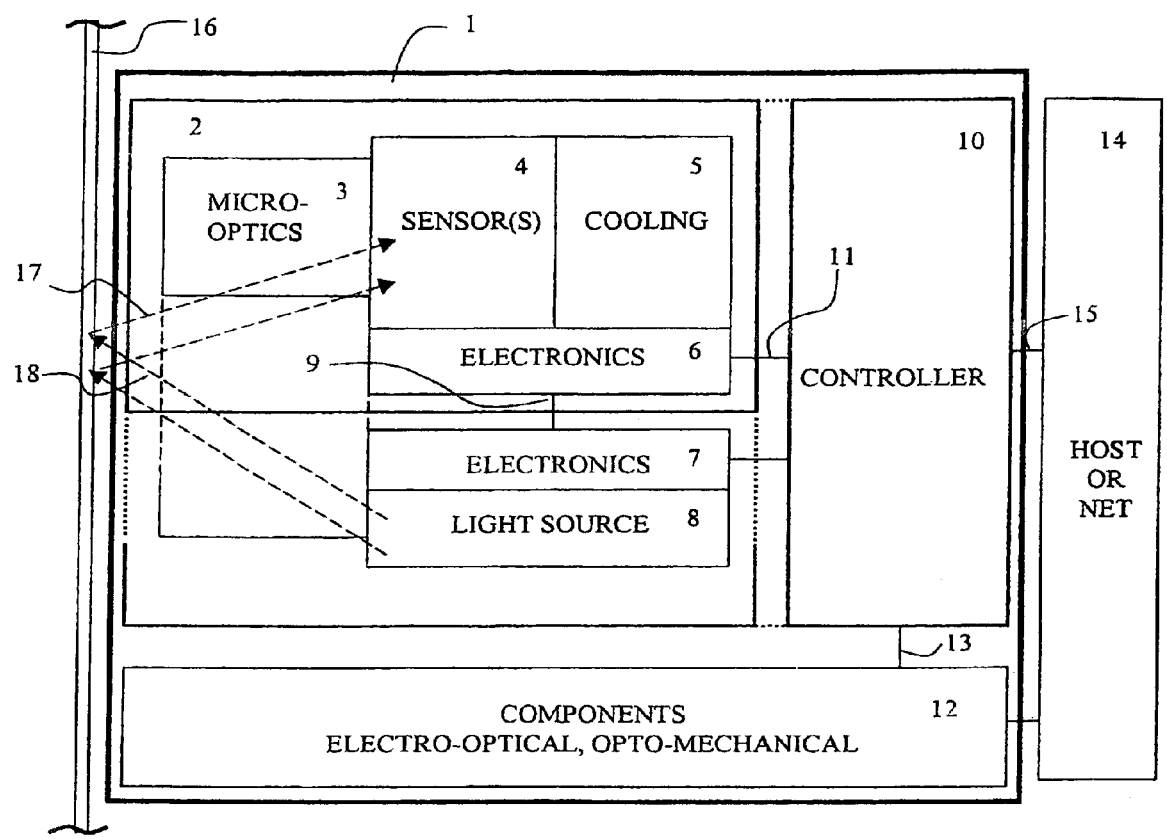
FIG. 1 shows an overview of an embodiment of the apparatus according to this invention in block diagram form.
FIG. 2 shows an embodiment of a micro-optical design for the apparatus according to this invention which allows the use of a single or a plurality of available array sensors.

The present invention provides an apparatus and methods for photo-electric measurement such as imaging and spectroscopy from objects which present large areas. The apparatus particularly provides miniaturized optics and/or optical component arrays with a single or a plurality of optical sensors, preferably image sensors, and other related components such as light sources into a compact and sensitive optical measurement unit. Any desired size of the area to be measured is accommodated, with consistent performance over the entire area, selectable spatial and spectral resolution and high speed. "Hyperspectral" imaging/measurement in up to six dimensions can be performed—with high resolution in two dimensions (area) or three spatial dimensions (volume), intensity, wavelength and time. In particular, the higher speed operation enabled by this invention allows adequate resolution in the time axis for many applications such as the measurement of chemical reaction kinetics. The invention is also suitable for spectral measurement and/or imaging of a plurality of objects which are widely spaced (including in arrays or "arrays of arrays") within a relatively large area. Gated fluorescence spectroscopy and/or fluorescence lifetime measurements are possible. The apparatus is capable of operating in various modes and combinations thereof, such as imaging, scanning "Time Delayed Integration", scanning spectroscopic, or confocal.

The apparatus or a plurality thereof is preferably used in conjunction with, or integrated with, a "controller", which is preferably the "intelligent detector" and image sensor device(s) according to Patent Application No. PCT/EP01/11027 filed on Sep. 24, 2001, titled "Image Sensor Device, Apparatus and Method for Optical Measurements". The invention thereby enables high-speed real-time adaptive sensing with closed-loop feedback controls. As a particular example, measurements from surfaces which are uneven or tilted with respect to the optical measurement unit can be performed, since real-time adaptation (e.g. of focus) is enabled. The functionality and operational modes of the apparatus, particularly the individual readout mode(s) of the sensor(s) and acquisition timing, are real-time programmable by the said intelligent detector.

According to a preferred embodiment of the invention multiple CM-CCDs are used as needed for any specific configuration. The CM-CCDs can be cooled and hermetically sealed in a multi-chip module if necessary. The data streams from the CM-CCDs are combined in the camera into one interface to the host. With optional data processing in the camera (e.g. via hardware logic or a Digital Signal Processing (DSP) system) data can be immediately reduced and the information content maximized. For example, all pixels with no information content can be immediately discarded, and the sample information reduced to essential results such as the intensity, standard deviation, etc.

According to a first approach the invention performs parallel imaging of each Region-Of-Interest (which may correspond to "wells" of a microplate) with a high resolution. For each well, a dedicated miniaturized optical system and CM-CCD device is used. According to the required throughput vs. cost constraints, this system is modularly duplicated into an array. A cost-effective implementation is to image one row of wells at a time, and to step (index) through all rows in the other direction. For a 96-well Microplate format, either 8 or 12 spots would be imaged simultaneously. There are two techniques to perform imaging: "Step-scan imaging" and "Time Delay Integration". Step Scan Imaging, a parallel row of CM-CCDs take "snapshots" of each row of wells. Either the plate or the detection system is stepped until all rows are measured. Note that the frame transfer architecture of the CM-CCD allows to integrate the next row while reading the current one—this increases the "light collection duty cycle" and therefore the overall sensitivity. The CM-CCD would image each well at its highest resolution and highest frame rate. In the Time Delayed integration mode, the scanning occurs continuously, and the rows of the CM-CCD are synchronized to and clocked synchronously with the mechanical scanning.

According to a second approach the invention performs hyper-spectral scanning of each well. Hyper-spectral scanning has the advantage that the spectrum of the emission is digitized. A line is excited, and the emission spectrum of the line is measured. It is possible to select the wavelength bands or change them on-the-fly. The signal in these bands are binned (summed) directly on-chip, thereby increasing sensitivity and speed, and greatly reducing data volume. In this approach, each well is scanned using a CM-CCD, where the vertical dimension of the CM-CCD is used as the spectral axis. The horizontal dimension of the CM-CCD is the spatial axis. It represents the "width" of the scan—i.e., the width of the well. This requires that the emission optics include a spectrograph, typically a diffractive element. The use of miniaturized optics and optical arrays is appropriate. The most likely scheme for spectral scanning is to scan one dimension of the plate at a time. Speeds achievable for continuous scanning of spectra are for example for continuous reading one wavelength band 5000 frames/s or for continuous reading four wavelength bands 3000 frames/s.

Again, the frame transfer architecture of the CM-CCD allows to integrate the next line while reading the current one—this increases the "light collection duty cycle" and therefore the overall sensitivity.

FIG. 1 shows a block diagram of an embodiment of the apparatus 1 according to this invention in a typical application. Referring to FIG. 1, the apparatus 1 performs optical measurements of the area or volume presented by the target object 16. The apparatus comprises an optical measurement unit 2, consisting of a "micro-optical system" 3, a single or a plurality of sensor(s) 4, preferably image and/or array sensor(s); an optional system 5 for cooling and/or temperature stabilization of the sensor(s); sensor electronics 6 and, when present, the cooling system. The micro-optical system is a compact optical system which, in its most preferable form, integrates one or any combination of refractive, diffractive, reflective, absorptive elements, fiber optical, and/or spatially filtering elements, and/or one or more arrays thereof. Particularly, it may include micro-lenses, spatial light modulators such as liquid crystal (LCD) and micro-mirrors, and/or one or more arrays thereof. Furthermore, the optical functionality of the micro-optical system may be spatially variable, such that measurements of various types can be simultaneously performed. For example, imaging of the target object or portions thereof may be performed in particular location(s), simultaneously with spectral measurement in another location. The apparatus may additionally comprise a light source 8 such as a laser, laser diode, lamp, or the like; and its related electronics 7, which may be electrically connected 11 to a controller 10 and/or electrically connected 9 to the sensor electronics 6. The apparatus may also additionally comprise a controller 10 and/or components 12 which may influence the measurements. The controller preferably has a high-speed interface 11 to the optical measurement unit 2 as well as the components 12, in order to perform real-time adaptive functions. The controller further provides communication 15, for example preferably with a host computer or network 14. Generally, the target object may be excited (illuminated) via an optical path 17 by the light source, and the measurement is performed by the sensors via a light collection path 18. The said excitation optical path may preferably include the said micro-optics or may be associated with a separate optical system, may be incident on the object to be measured from any direction, including paths coaxial or partially coaxial with the collection path.

FIG. 2 shows an embodiment of a micro-optical function of the apparatus according to this invention which allows the use of a single or a plurality of available array sensors. Referring to FIG. 2, one axis of measurement is shown, whereby the same concept applies to any number of axes. The micro-optic system 3 allows any desired length of the axis(axes) of measurement on the object 16 in that it optically separates optical signal from along the said axis/axes into a plurality of smaller segments. Light from each of these segments is then measured by an array sensor. The segments of light $21_1$ to $21_n$ at the sensor are preferably projections of corresponding adjacent or overlapping segments $20_1$ to $20_n$ on the object being measured. This enables the use of "available array sensors" $4_1, 4_2, \ldots 4_n$. i.e., those which are readily commercially available as opposed to custom-made or application-specific, since it permits space between the active areas 22 of the sensors. "Available array sensors" typically consist of semiconductor die(s) which are housed in an integrated circuit package. When such sensors are placed adjacent to each other in an array as close as possible, there is significant space between the active sensitive areas. Alternatively, "buttable" array sensors, which can be arranged in such close proximity to each other so as to minimize the dead space between their active areas, may be used. The magnification of the system may be less than one, as implied by the dashed lines representing light paths in FIG. 2, or may be one or greater. This implies that very high resolution measurements of the area can be achieved.

Since the functionality of the measurement unit may be spatially variable, sample information can be acquired from the sample carrier or from the samples themselves (e.g. reading barcodes using scanning imaging mode) while spectral measurement of the samples is simultaneously performed.

Such a compact measurement unit which scans in one axis lends itself to robotics and high throughput processing of arrays of sample carriers. Since it is not a large optical system in a fixed position, it allows for convenient access to the sample carrier(s) for other processes such as pipetting, chemical processing, electrical contacting, fluidics and the like.

Figure 3:
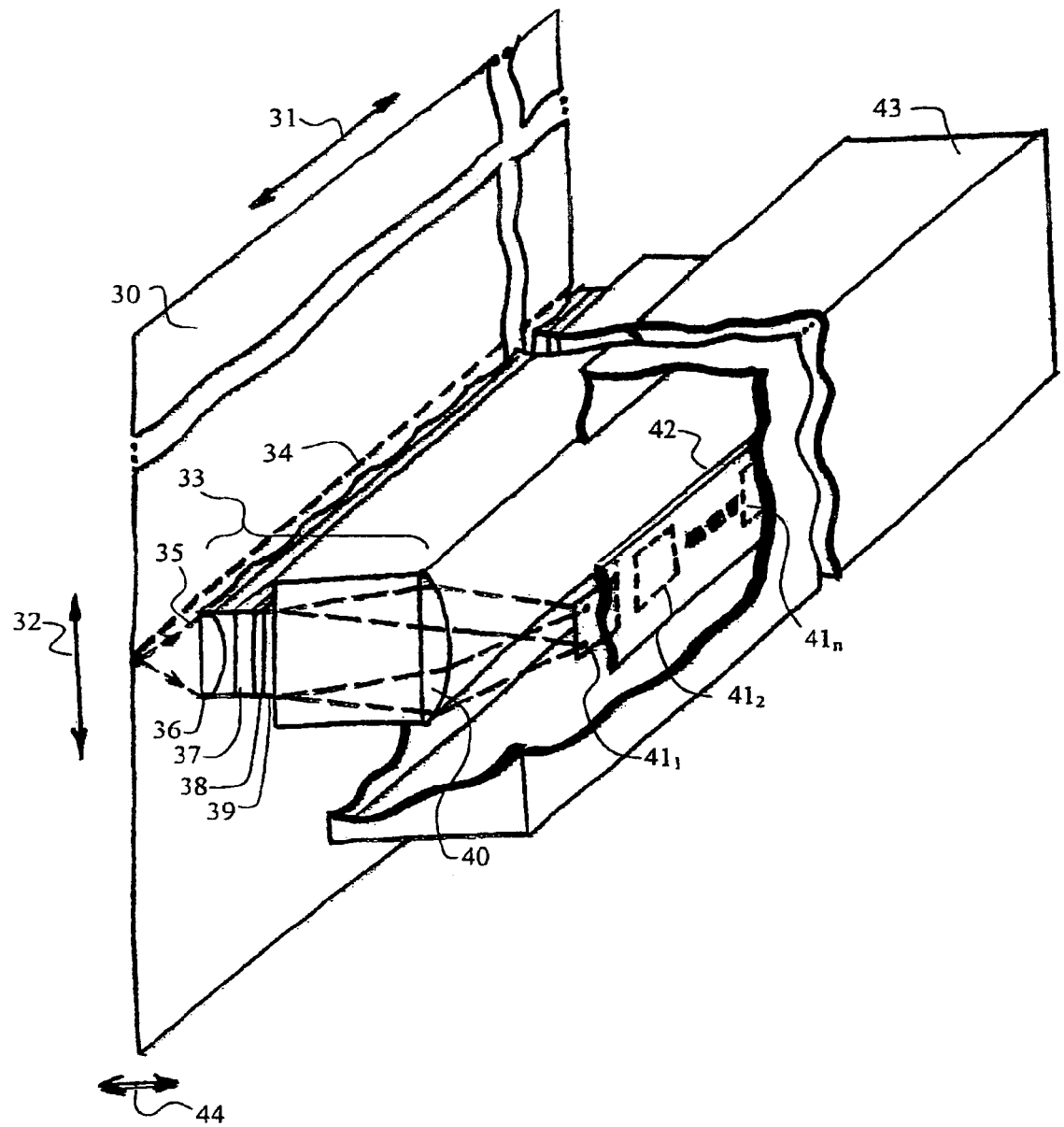
FIG. 3 shows an embodiment of the micro-optical measurement unit of the apparatus according to this invention.
Figure 5:
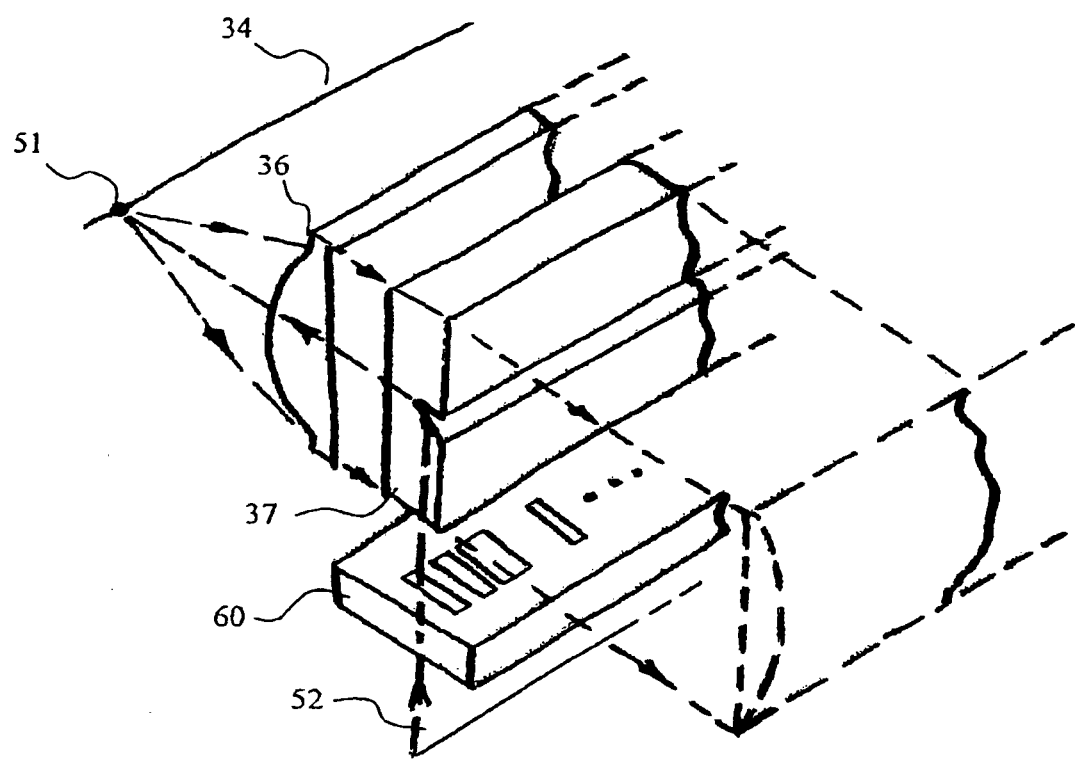
FIG. 5 shows an embodiment of a micro-optical measurement unit of the apparatus according to this invention whereby excitation (illumination) of the target object is variable through spatial light modulation.

FIG. 3 shows an embodiment of a micro-optical measurement unit of the apparatus according to this invention which can accommodate any desired size of the area 30 to be measured. Two or three dimensional imaging and/or "hyperspectral" imaging is performed by the mechanical movement of the measurement unit along one axis 32, and a modular expansion of the measurement unit in a second axis 31. Three dimensional (volume) measurement may be achieved preferably through the use of confocal optics (as described in FIG. 4), which allows the measurement to be limited to a particular depth of focus in a third axis 44. As shown, measurement is performed at the position indicated by the dashed line 34 (hereto "measurement line") on the measurement area, this line spanning any desired length of the axis 31. In this axis, the optical signal to be measured is segmented as described in conjunction with FIG. 2 by the micro-optical system 33 (micro optics 3). The said measurement line may be wholly or in part optically excited (illuminated), whereby the said excitation may be incident onto the area from any direction. The micro-optical measurement unit comprises a micro-optical system 33, a single or a plurality of array sensors $41_1, 41_2, \ldots 41_n$, optional thermoelectric (Peltier) cooling 42 for the sensor(s), a housing 43 and related electronics (6; FIG. 2). The micro-optical system efficiently collects optical signal from the measurement line as shown by the rays 35 via a light collecting means 36 with high numerical aperture. The micro-optical system may include:

a) a means 37 for coupling excitation light through the micro-optic system and onto the measurement line as described in conjunction with FIG. 5, b) a means 38 of selectively filtering unwanted light, such as absorptive, reflective, or interference optical filters, or the like, c) a means 39 of separating the light into its wavelength components, such as a grating or prism, or the like.

The micro-optical system further comprises a focusing means 40 for focusing the collected light onto the sensor(s). The housing provides a rugged, mechanically precise and stable basis for the measurement unit. The micro-optical system is preferably an integral part of this housing, forming an enclosure and functioning as an optical port or window. Furthermore, the micro-optical system may be hermetically sealed onto the housing.

The sensor(s) may be cooled and/or temperature stabilized, preferably by thermoelectric (Peltier) cooler(s). In embodiments where the sensor is cooled below a particular temperature, the said enclosure is hermetically sealed. The sensor related electronics may be inside or outside the said enclosure, or both. Its preferred functionality includes communications, power supply, timing controls, drivers, temperature measurement and regulation, signal processing, input/output and control functions. The optical signals are preferentially measured by an image sensor such as a CCD (Charged Coupled Device), CMOS (Complimentary Metal Oxide Semiconductor), CID (Charge Injection Device), or the like. In order to maximize performance, sensor features including one or more of the following are preferred:

a) Fast clearing of all or a portion of the pixels, such as the clearing of the entire device and/or the serial (readout) register with a single pulse.

b) Frame Transfer or Interline transfer architecture, for increased light collection duty cycle and decreased blurring.

c) Random access to pixels increases speed and allows real-time adaptive sensing.

d) Microlenses to increase full factor.

e) Multiple serial registers, split serial registers and/or multiple outputs increase speed.

f) High shift rates in both horizontal and vertical directions, enabled by sensor features such as metal strapping of gates and polysilicon connections, reduction of distributed resistances and capacitances of connections, driving signals on the chip from multiple locations.

g) Summing wells at each output, which allow programmable pixel binning without noise penalty.

h) Anti-blooming in the active area, storage area and/or serial register(s).

i) Segmentation of the device(s) into a plurality of sub-areas of pixels, whereby the sub-areas may be read and/or controlled individually and/or simultaneously.

Figure 4:
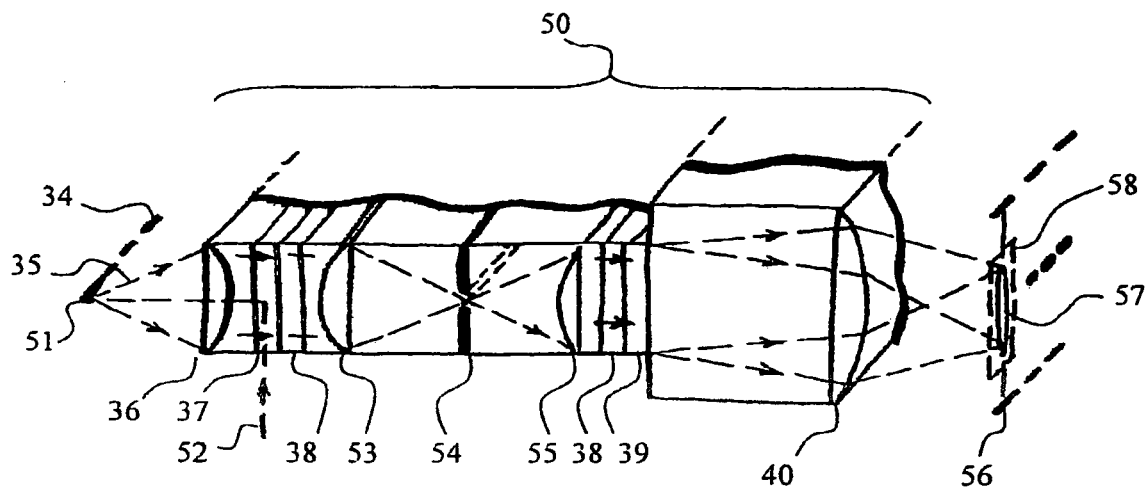
FIG. 4 shows an embodiment of a micro-optical design of the apparatus according to this invention for confocal measurement.

FIG. 4 shows an embodiment of a micro-optical system design 50 of the apparatus according to this invention for confocal measurement. Here only the functions additional to those in FIG. 3 are described. In this embodiment, the light collected from the measurement line is re-focused by a focusing means 53. At this focal point, a means of spatially filtering 54, preferably in the axis perpendicular to the measurement line, is placed. This means of spatially filtering preferentially consists of a spatially varying layer (mask) which selectively prevents light from continuing on to the sensor, and may accomplish this function by means of absorption, reflection, refraction, and/or diffraction. The light is collimated by a means 55, may be further filtered by a filtering means 38, may be separated into its wavelength components by a means 39, such as a grating or prism, or the like. The resulting optical signal to be measured is focused onto the sensor(s) at the plane 56. As depicted in FIG. 4, the spectrum (spectra) 57 originating from point(s) 51 on the target object is/are preferentially measured by one or a plurality of region(s) on the sensor 58, whereby the corresponding sets of pixels can be programmably defined or changed in real time. The signal contained by these pixels may be "binned" or summed on-chip. The sets of pixels may represent various wavelength bands from samples being measured. The said programmable region(s) allow spatial filtering in two dimensions of the signal from desired point(s) on the measurement line.

FIG. 5 shows an embodiment of a micro-optical measurement unit of the apparatus according to this invention whereby excitation (illumination) of the target object is variable through spatial light modulation. This is particularly useful for adaptive optimization of the excitation of samples, which is a method of increasing the consistency and dynamic range of measurement, and for selective photochemistry (e.g. catalyzing of reactions). Excitation (illumination) light 52 preferably following a path with the form of a line is spatially filtered in one or two dimensions by a filtering means 60 and focused onto the measurement line 34. The spatial light modulation is preferably real time programmable. This excitation light may be preferentially coupled through the micro-optic system by a coupling means 37, which influences the light by means of reflection (e.g. mirror, dichroic filter), grating, and the like. The said programmable spatial filtering is preferably a "spatial light modulator" (SLM) which is preferably an integral part of the micro-optic system, which may utilize Liquid Crystal Display (LCD) technology, micro-mirrors, acousto-optics, or the like, and which may be capable of varying the intensity of the transmitted light. The excitation light may be spatially continuous along the direction of the measurement line 34, may consist of a single or a plurality of beams, and/or the said beams may be mechanically moving (scanning).

Figure 6:
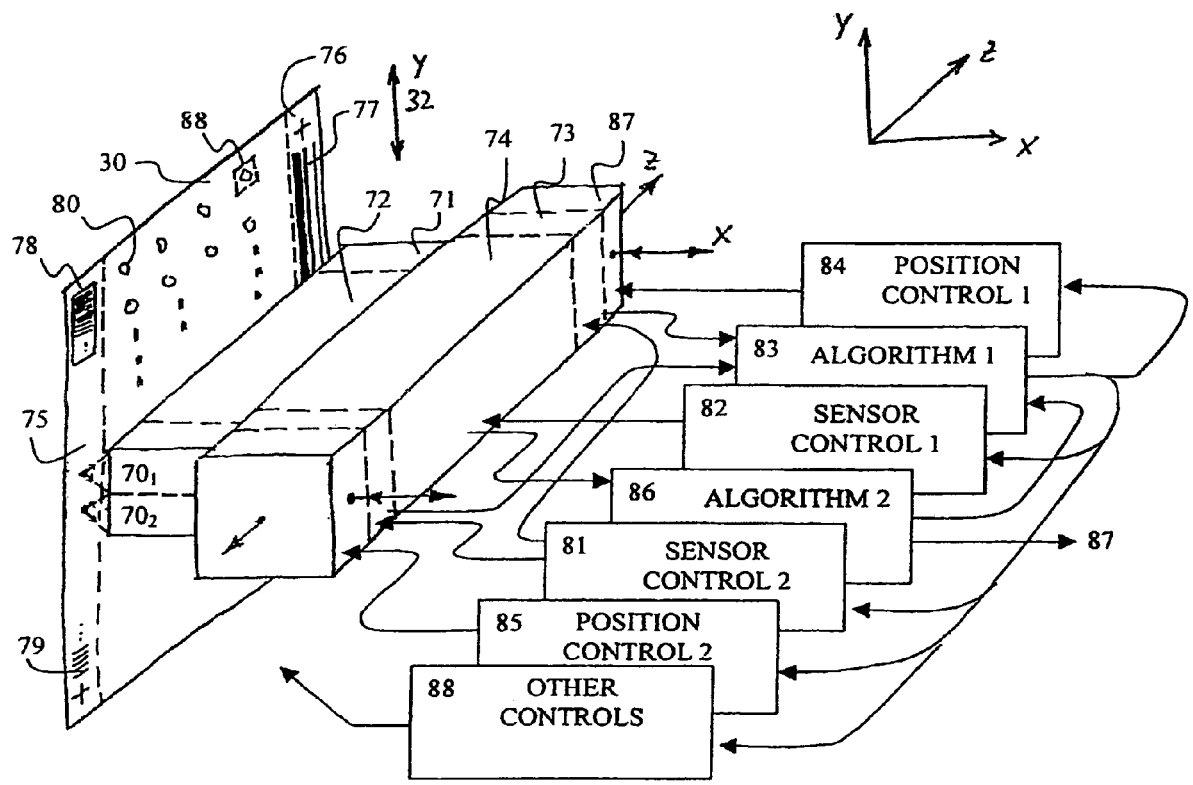
FIG. 6 shows an embodiment of the micro-optical measurement unit of the apparatus according to this invention with simultaneous multiple mode operation, which enables real-time adaptation.

Referring to FIG. 6, this embodiment of the micro-optical measurement unit illustrates simultaneous multiple mode sensing operation. This enables real-time adaptation during the measurement process, providing benefits such as:

a) optimization of the measurement via methods such as automatic positioning (X, Y and focus) of the measurement unit, location of samples and corresponding adaptation of the readout mode(s) and acquisition parameter(s) of the sensor(s).

b) measurement from tilted areas (non-parallel to the plane of movement of the measurement unit)

c) acquisition/modification of information from the sample carrier and/or from the samples themselves simultaneously while measuring the samples. This sample information may also be used in real-time to optimize the measurements. The measurement unit measures the target object or sample carrier 30 via movement in the direction 32. The target object preferably incorporates one or a plurality of particular area(s) 75 which provides the apparatus read and/or write access to information. A first portion or multiple first portions of the optics 71 and corresponding sensing 73 of the measurement unit is/are applied to acquiring information from features on the target object, such as fiducials 76, markings 79, reference signals 80, barcodes 78, and the like. In the example shown in FIG. 6 both sides of the measurement unit comprise a first portion. Second portion(s) of the optics 72 and corresponding sensing 74 of the measurement unit may be applied to the simultaneous, optimized measurement of samples. The measurement unit preferably may be spatially positioned with respect to the target object by positioning means 87, which is preferably under high speed feedback control of the controller of the apparatus. The functionality denoted by blocks 81 through 86 is implemented in the electronics 6, 7 and controller 10 of the apparatus, as described with FIG. 1. Two measurement lines are depicted, with corresponding optics 70, and 702, whereby a single or a plurality of measurement lines may also be implemented. As a first example, the apparatus can scan (image) fiducial markings on the target object, thereby calibrating the location of samples.

This information is processed by an algorithm 83. The measurement of the samples can immediately be optimized by programming the sensor(s) readout modes optimally via sensor controls 81, 82, by position control 84 and 85, and/or by controlling other parameters 88 such as light source. The samples are therefore more optimally measured, whereby the results can be further processed by a second algorithm 86. For example, the set of pixels on the image sensor containing light from each sample 88, or from each desired wavelength bandwidth of each sample, can be determined in real-time (during the measurement process), and summed on-chip ("pixel binning") in order to increase sensitivity.

As a second example, the apparatus can measure features on the target object such as stripes 77 in the scan direction to gain focus and positional information. The apparatus then performs real-time positional adjustment via position adjustment means 87 to "track" the uneven surface, optimizing its spatial position (particularly focus) relative to the target object.

As a third example, the apparatus includes two or more positions (lines) of measurement, sequentially positioned in the scan direction. This allows a high degree of measurement optimization, since the following measurement line(s) can use the apriori information from previous measurement lines for optimization. For example, a first measurement line performs imaging of the target object. These images are immediately processed, and the information used to optimize the measurement system before a second measurement line performs measurements. Parameters such as focus, scan speed, excitation intensity, exposure time, sensor readout mode and the like can be optimized.

Furthermore, multiple measurement lines allow imaging and spectral measurement of the area to be done in one scan.

Figure 7:
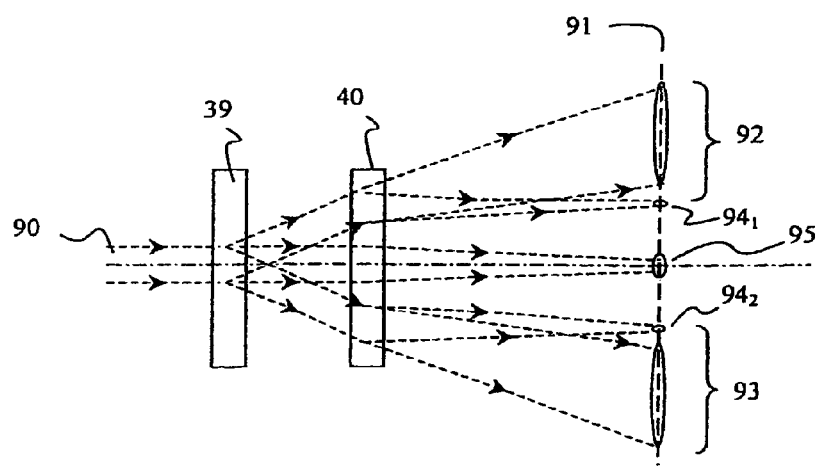
FIG. 7 shows an embodiment of a means for separating light into its wavelength components based on the use of a binary grating.

FIG. 7 shows an embodiment of a means for separating light into its wavelength components based on the preferable use of a simple one-level binary grating 39. The slits of such a grating may be created lithographically using a single mask (e.g. by e-beam lithography), and may be inexpensively replicated. The grating separates a collimated beam of light 90 into a "two-sided spectra", comprising essentially of the zeroth 95, plus one 93 and minus one 92 spectral orders. These are focused onto a sensor plane 91 by a focusing means 40. A typical Laser-induced fluorescence spectral pattern is depicted in FIG. 7, whereby the laser wavelength is shown by $94_1$ and $94_2$. It is known that approximately 40% of the incident energy is contained in the plus one spectral order, and 40% in the minus one order. By collecting both of these orders, an overall efficiency of approximately 80% can be achieved, which is typically better than state-of-the-art blazed holographic gratings. Furthermore, such simple binary gratings are particularly suitable for integration into micro-optical systems.

FIGS. 8 through 14 show various embodiments of the means of acquiring two-sided spectral information using image sensor(s), whereby one of possibly a plurality of sensors is shown. Two sided spectra are shown projected onto the active (light sensitive) area 100, although this may be any image generated by the measurement unit. The plus one and minus one spectral orders are projected onto areas $98_1$ and $98_2$, whereby the spectra originating from individual samples are shown by $106_1, 106_2, \ldots 106_m$ The spectra of each sample may be measured using one or a plurality of programmable sub-areas 101. Since the plus one and minus one orders are mirror images of each other on the sensor, these two halves of the spectrum to be measured may be recombined (added together) either by charge combination (pixel binning) on-chip, by analog summing in the sensor's signal chain, by digital summing in the controller of the apparatus, or by software image processing. In the case of CCD sensors:

a) Serial (readout) registers are shown by 102 and 103, whereby the dashed lines indicate optionally present features.

b) Each serial register may be sub-divided into a plurality of segments $104_1, 104_2, \ldots 104_n$, with outputs $105_1, 105_2, \ldots 105_n$.

c) A summing well at each output, as well as a means for fast clearing of the serial register, such as single pulse clearing into a charge drain, are preferable.

Figure 8:
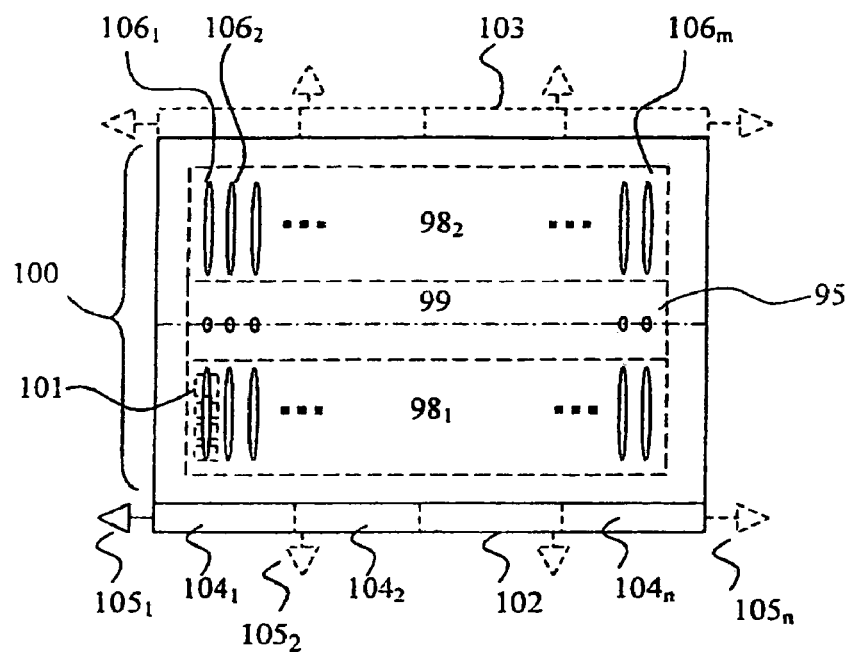
FIG. 8 shows a first embodiment of a means of acquiring two-sided spectral information using image sensor(s)
Figure 9:
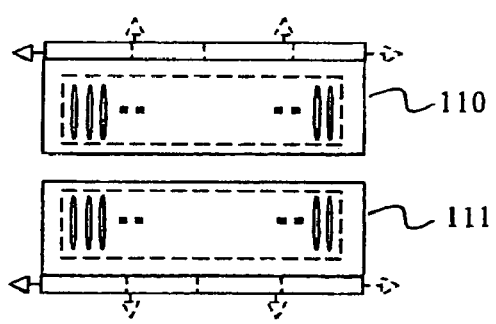
FIG. 9 shows a second embodiment of a means of acquiring two-sided spectral information using image sensor(s)

Referring to the first embodiment in FIG. 8, the image sensor shown may be a full-frame or interline transfer type CCD. The latter is preferred in this embodiment since it allows higher light collection duty cycle at higher frame rates, has electronic shuttering capability, and reduces blurring. In the case of two-sided spectra, the zeroth order 95 located in the area 99 may be ignored, or may be used as a locating and calibrating means, or as an input for real-time adaptation for optimizing measurements. The two spectral orders can be measured simultaneously. Referring to the second embodiment in FIG. 9, the plus one and minus one spectra may be measured using separate image sensor devices 110 and 111. This mainly reduces the sensor area in cases where the distance between the first orders is substantial.

Figure 10:
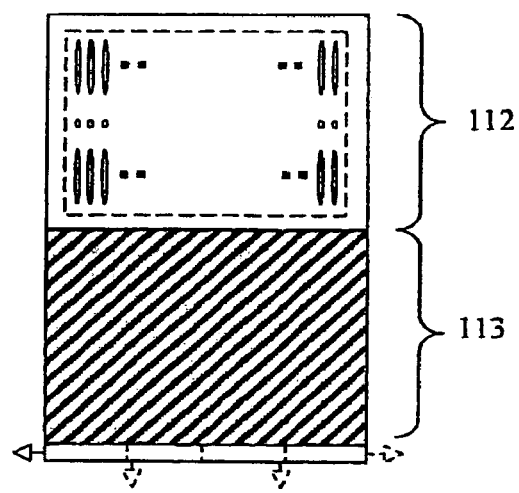
FIG. 10 shows a third embodiment of a means of acquiring two-sided spectral information using image sensor(s)

Referring to the third embodiment in FIG. 10, a frame transfer type CCD may be used to acquire the two-sided spectral information. The active region 112 is exposed, then shifted quickly under the shaded region 113 (electronic shuttering action). As the shaded region is read via the serial register, the next exposure occurs in the active region.

Figure 11:
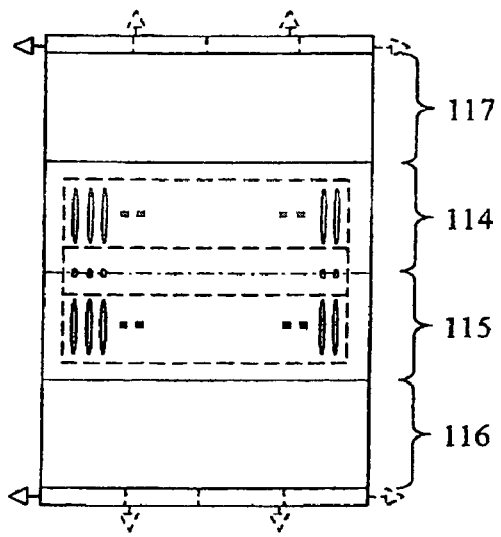
FIG. 11 shows a fourth embodiment of a means of acquiring two-sided spectral information using image sensor(s)
Figure 12:
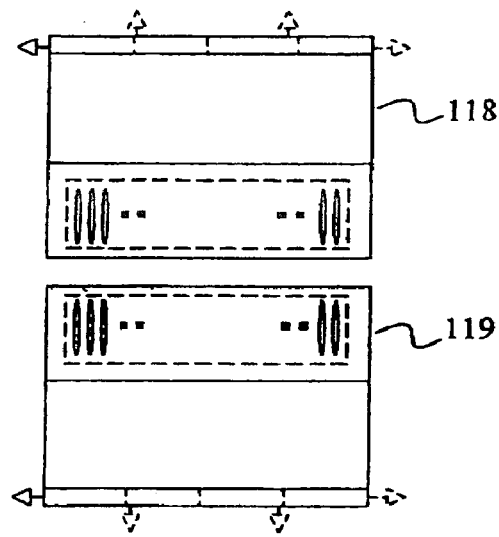
FIG. 12 shows a fifth embodiment of a means of acquiring two-sided spectral information using image sensor(s)

Referring to the fourth embodiment in FIG. 11, a frame transfer type CCD with two shaded regions 116, 117 may be used to acquire the two-sided spectral information. The active region is divided into two separately controllable regions 114 and 115. In this case, two spectral orders can be measured simultaneously. Referring to the fifth embodiment in FIG. 12, two frame transfer type CCDs 118 and 119 may be used to acquire the two-sided spectral information.

Figure 13:
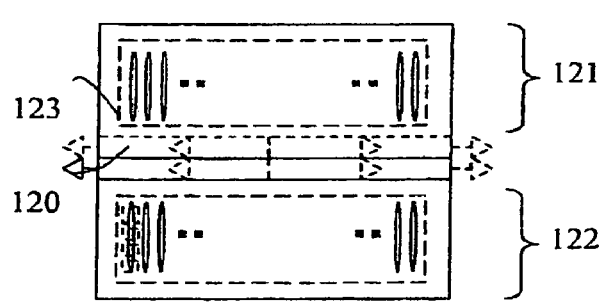
FIG. 13 shows a sixth embodiment of a means of acquiring two-sided spectral information using image sensor(s)

Referring to the sixth embodiment in FIG. 13, the image sensor shown may be a full-frame or interline transfer type CCD, whereby one or two serial register(s) 120, 123 are positioned between the spectral orders to be measured. Light from the zeroth order is prevented from being collected by the sensor by a means such as an aluminium mask on the sensor, or by blocking the light off-chip; i.e. by blocking the light by means of a mechanical mask or aperture which is not integrated onto the photo-electric conversion device(s). The spectral halves 121, 122 may be recombined (binned) directly on-chip in the serial register during the readout process.

Figure 14:
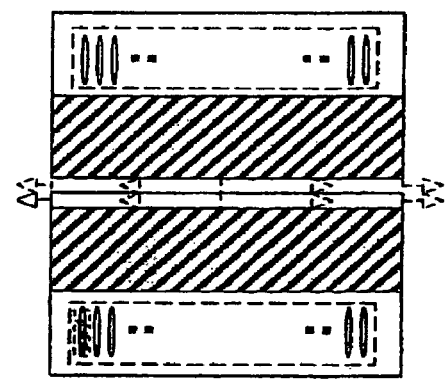
FIG. 14 shows a seventh embodiment of a means of acquiring two-sided spectral information using image sensor(s)

Referring to the sixth embodiment in FIG. 14, a frame transfer device may be used as described in relation to FIG. 13.

Figure 15:
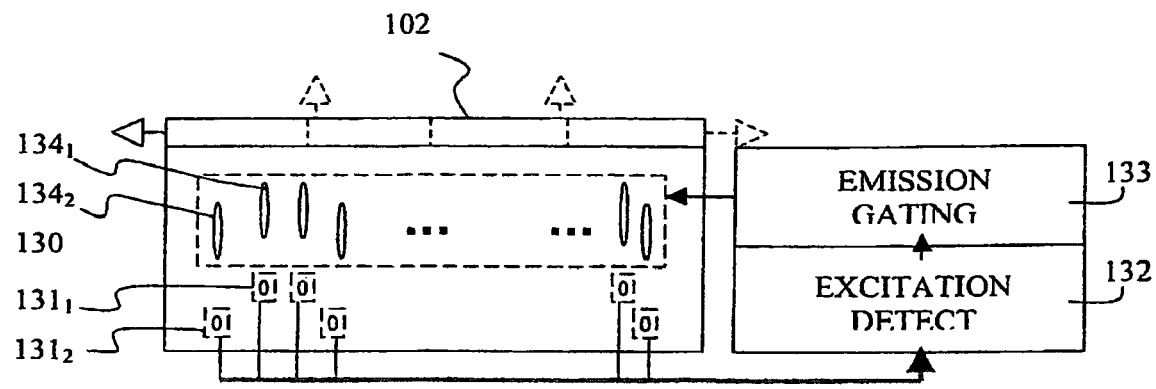
FIG. 15 shows an embodiment of a means of performing gated detection using image sensor(s)
Figure 16:
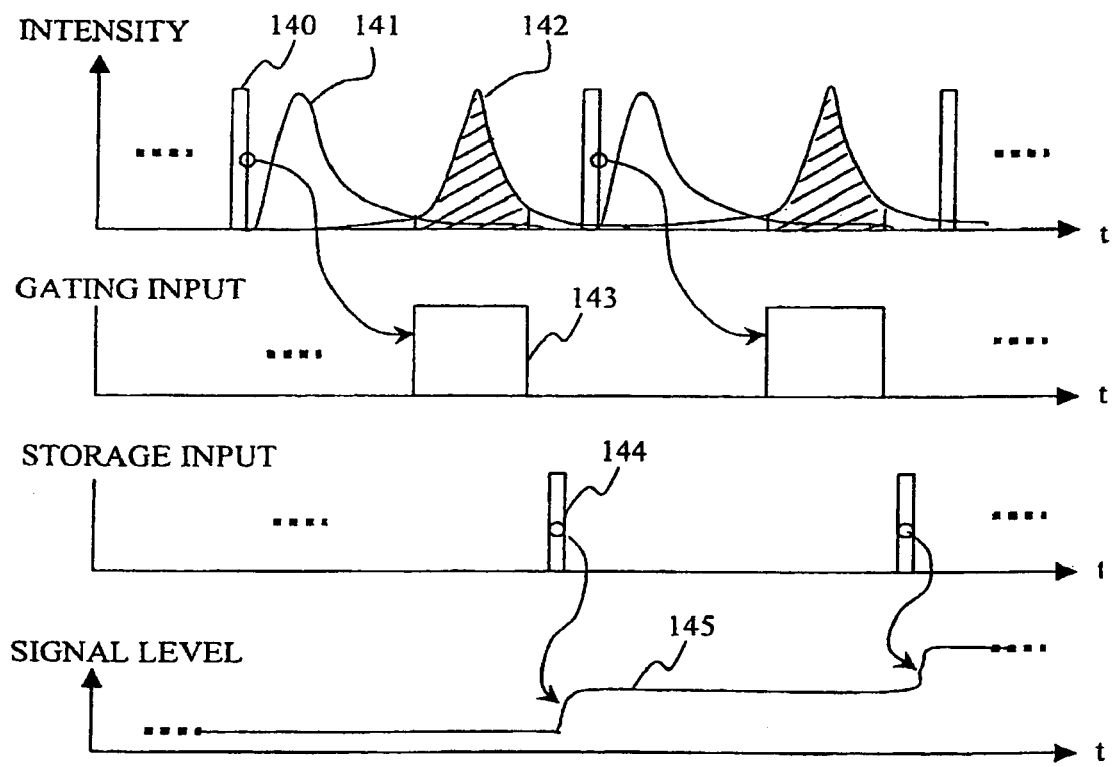
FIG. 16 shows an embodiment of a method for performing gated detection.

FIGS. 15 and 16 shows an embodiment of a means and a method of performing gated detection using image sensor(s). Such time gated fluorescence or luminescence measurements combined with spectral discrimination effectively eliminates background autofluorescence and luminescence, resulting in more sensitive measurements. FIG. 15 shows an embodiment of time gating at the sensor, and FIG. 16 shows an example of a related time sequence of events during measurement (light collection). Typically a light source with particular wavelength characteristics is pulsed 140 for a short time to excite the samples. Undesirable emitted light (e.g. background autofluorescence) 141 and the emitted light 142 to be measured are shown having varying time delays. The excitation light is sensed by one or a plurality of sensing means $131_1$, $131_2$, ... $131_n$, and detected by a detection means 132. The sensing means and/or the detection means may preferably be integrated on the image sensor chip or may be implemented off-chip in the measurement unit. Based on the detection of this excitation light, the detection means generates a "gating input" signal 143 to an acquisition control means 133, which then enables (gates) the acquisition of emission spectra by the image sensor. After the majority of the desired emission is acquired in an active area, the acquisition control means then stores or adds 144 this signal to others previously collected in a storage region which is shielded from incident light. The signal level acquired 145 in this storage area therefore increases with every excitation pulse. At the end of the measurement time, the storage region is read. Discrimination between background autofluorescence and desired emitted signal can also simultaneously be performed based on their spectral differences. Furthermore, the said active areas and corresponding storage areas may be implemented on a pixel basis.

Since the time delays involved typically range from a few nanoseconds to hundreds of microseconds, the speed of operation of the excitation sensing, gating and acquisition control means is maximized by preferably integrating these on the image sensor itself, or alternatively very close to the sensor in the measurement unit.

An example of the application of this invention for spectral measurement of a plurality of objects which are widely spaced within a relatively large area is the simultaneous measurement of multiple electrophoresis micro-channels on a microplate or "lab-on-chip". In this case, the measurement unit may include a minimum number of small image sensors arranged along a first axis to acquire the number of measurement points in a row along this axis. In a second axis, the measurement unit is moved in steps, between rows of measure points. By using a repetitive scanning motion over the area, all measurement points can be simultaneously measured with a particular sample rate. This rate can be increased by modularly increasing the number of measurement units operating in parallel. Using the real-time features and multi-mode operation of this invention as described above, the measurement quality can be improved—for example by optimally positioning excitation into micro-channels using the sensor and/or automatically focusing and adapting to tilted surfaces during the measurement process. Specific embodiments of an apparatus and method for photo-electric measurement according to the present invention have been described for the purpose of illustrating the manner in which the invention may be made and used. It should be understood that implementation of other variations and modifications of the invention and its various aspects will be apparent to those skilled in the art, and that the invention is not limited by the specific embodiments described. It is therefore contemplated to cover by the present invention any and all modifications, variations, or equivalents that fall within the true spirit and scope of the basic underlying principles disclosed and claimed herein.

What is claimed is:

1. An apparatus for photo-electric measurement comprising:
   a) a single or a plurality of photo-electric conversion devices, including array sensor(s);
   b) an optical system comprising modules which are arranged and expandable in one axis or a plurality of axes in order to acquire electromagnetic radiation from a correspondingly modularly increasing length of a line or area on an object, with any desired resolution, wherein the said optical system spatially separates the said electromagnetic radiation modularly into a plurality of smaller segments, and projects electromagnetic radiation corresponding to the said smaller segments onto said single or a plurality of individual photo-electric conversion devices, wherein said smaller segments of electromagnetic radiation originate from adjacent regions of the line or area on the object, said adjacent regions partially overlapping such that contiguity is achieved; and
   c) sensor electronics related to said photo-electric conversion device(s) which enable the operating mode and functionality of said photo-electric conversion device(s) to be defined and changed in real-time, whereby functions are fully programmable, and said photo-electric conversion devices operate and/or are controlled independently and/or simultaneously.

2. The apparatus according to claim 1, wherein the said segments of electromagnetic radiation originate from a plurality of regions on the line or area to be measured, whereby the regions are adjacent to each other, or there is space corresponding to regions of no measurement interest between the said regions, wherein the apparatus provides its functionality only for regions to be measured.

3. The apparatus according to claim 1, wherein said optical system provides a magnification which is more than, equal to, or less than one.

4. The apparatus according to claim 1, wherein said photo-electric conversion device(s) comprise a plurality of readily available, off-the-shelf array sensors positioned adjacent to each other, wherein said array sensors comprise semiconductor die(s) which are housed in an integrated circuit package.

5. The apparatus according to claim 1, wherein said photo-electric conversion device(s) comprise a plurality of buttable array sensors positioned adjacent to each other, being stackable side-to-side such that there is minimum dead space between the active areas.

6. The apparatus according to claim 1, wherein said photo-electric conversion device(s) include any one or any subset of the following features:
  a) a means of clearing charge from the photo-electric conversion device(s) very fast,
  b) summing well(s) at each of the output(s) of the photo-electric conversion devices,
  c) metal strapped gates and connections to increase clocking speeds,
  d) thinned, back-illuminated CCD technology,
  e) low dark current "Multi-Pinned Phase (MPP)" operation mode,
  f) frame transfer architecture,
  g) interline transfer architecture,
  h) full-frame transfer architecture,
  i) charge amplification on the photo-electric conversion device;
  j) fiber optic bundle(s) directly bonded to the photo-electric conversion device,
  k) a single or a plurality of outputs,
  l) a single or a plurality of serial (readout) register(s),
  m) segmentation of the photo-electric conversion device(s), whereby all segments are read and/or controlled individually and/or simultaneously,
  n) integrated microlenses,
  o) anti-blooming in the active area, storage area and/or serial register(s),
  p) Charge multiplication integrated on the image sensor.

7. The apparatus according to claim 1, wherein said optical system comprises the integration of one or any combination of refractive, diffractive, reflective, fiber optical and spatially filtering micro-optical components, and/or one or more arrays thereof.

8. The apparatus according to claim 1, further comprising a cooling means, using thermoelectric (Peltier) device(s) for cooling and/or temperature regulating said photo-electric conversion device(s).

9. The apparatus according to claim 8, further comprising an enclosure which houses said cooled photo-electric conversion device(s) and related cooling means for preventing condensation on surfaces which are in the optical path, wherein said enclosure is hermetically sealed, and under vacuum or filled with an inert gas.

10. The apparatus according to claim 1, wherein said optical system forms an integral part of an enclosure which houses said photo-electric device(s).

11. The apparatus according to claim 1, wherein said optical system is factory pre-aligned spatially and spectrally with respect to said photo-electric conversion device(s).

12. The apparatus according to claim 1, further comprising a means of exciting (illuminating) the target object (30) with electromagnetic radiation wherein the focus thereof is factory pre-aligned spatially with respect to the said optical system and photo-electric conversion device(s) such that the measurement performance is optimized, wherein the said measurement performance comprises one or a plurality of the following: focal, spectral and spatial positioning and resolution; sensitivity; limit of detection, acquisition speed.

13. The apparatus according to claim 1, wherein excitation (illumination) electromagnetic radiation is acquired and said optical system includes a means for coupling into the optical system, and focusing said excitation (illumination) electromagnetic radiation at the line or area to be measured.

14. The apparatus according to claim 12, wherein the apparatus includes a means for spatially varying the said excitation (illumination) at the line or area to be measured, wherein said means is real-time programmable, integrated with the optical system, and uses LCD-, acousto-optic or micro-mirror-based spatial light modulator(s).

15. The apparatus according to claim 7, wherein all components of the apparatus are tightly integrated into a compact, miniaturized measurement unit, with all of said micro-optical components permanently fixed relative to each other and to said photo-electric conversion device(s), with no mechanical adjustments.

16. The apparatus according to claim 1, wherein the said optical system includes a means for spreading electromagnetic radiation according to wavelength, and projects the resulting spectra onto said photo-electric conversion device(s).

17. The apparatus according to claim 1, wherein the functionality of said optical system and said photo-electric conversion device(s) is variable, corresponding to the spatial location on the line or area such that for example measurements of various types can be simultaneously performed.

18. The apparatus according to claim 1, wherein said optical system is a confocal system, and comprises at least one spatial filter whereby electromagnetic radiation from a plurality of points on the line or area to be measured is spatially filtered at particular refocusing points and/or planes, and said spatial filter is implemented by a pinhole or slit which is implemented using absorptive, diffractive, refractive element(s), and/or is defined by one or a plurality of programmable sub-area(s) of pixels of said photo-electric conversion device(s).

19. The apparatus according to claim 16, wherein the apparatus is modularly expanded in a first direction to measure a particular length of a line on an area presented by a target object, and comprises means for moving, the apparatus in a stepped and/or scanned manner in a second direction in order to measure said area.

20. The apparatus according to claim 19, wherein said apparatus produces image(s) of an area or a plurality of sub-areas thereof, whereby said photo-electric conversion device(s) is/are operated in "Time Delayed Integration" mode, line scanning mode, or imaging mode.

21. The apparatus according to claim 20, wherein the electromagnetic radiation from the area to be measured, or sub-areas thereof, is separated into its wavelength components and projected onto said photo-electric conversion device(s) and wherein the spectral axis is perpendicular to the axis of movement of the apparatus.

22. The apparatus according to claim 16, wherein a plurality of measurement lines in said first direction are simultaneously measured, said measurement lines being positioned sequentially in the direction of movement of the apparatus.

23. The apparatus according to claim 16, wherein said means of spreading electromagnetic radiation according to wavelength comprises a binary grating with a single level or single mask binary grating, wherein the odd or minus one and even or plus one first order spectra are both acquired simultaneously by the apparatus.

24. The apparatus according to claim 23, further comprising combining means for combining said odd and even first order spectra on the photo-electric conversion device(s), during the readout process via pixel binning.

25. The apparatus according to claim 23, wherein said sensor electronics combines said odd and even first order spectra in analog manner.

26. The apparatus according to claim 23, wherein said sensor electronics combines said odd and even first order spectra digitally, in a real-time, in-line fashion.

27. The apparatus according to claim 23, wherein said controller combines said odd and even first order spectra digitally, in a real-time, in-line fashion.

28. The apparatus according to claim 1, wherein an excitation (illumination) source and related electronics are an integral part of the apparatus, whereby said optical system delivers electromagnetic radiation from said optical source to the object to be measured.

29. The apparatus according to claim 1 for "excitation gated" and/or "emission lifetime"—aided measurements, comprising:
   a) means for pulsing an excitation (illumination) source, whereby a measurement includes a single or a plurality of said pulses,
   b) means for sensing the electromagnetic radiation pulse at the wavelength band corresponding to the excitation (illumination) source and means for detecting the electromagnetic radiation pulse at the plane of the said photo-electric conversion device(s),
   c) means for collecting desired electromagnetic radiation by the active area of said photo-electric conversion device(s) only during a programmably defined time, relative to the excitation pulse, and
   d) means for integrating/summing the emission signal collected after each excitation pulse in shaded "storage" regions on the said photo-electric conversion device(s), which are read after a single or a plurality of excitation pulses, wherein said collecting means and said integrating/summing means are implemented on an individual pixel basis.

30. The apparatus according to claim 29, wherein the sensing means, detecting means, collecting means and integrating/summing means, as well as all related circuitry are integrated onto the said photo-electric conversion device(s).

31. The apparatus according to claim 29, wherein the sensing means, collecting means and integrating/summing means are integrated on separate photo-electric conversion device(s), and the pulsing means and the detecting means are located in close proximity to the photo-electric conversion device(s).

32. The apparatus according to claim 1, further comprising a means of mechanically moving and/or positioning the apparatus in up to three dimensions with respect to the object to be measured, wherein the said means of positioning is further controllable by said controller in real time during measurement.

33. The apparatus according to claim 1, further comprising a controller, and an intelligent detector, wherein said controller is an integral part of the apparatus.

34. The apparatus according to claim 33, for use with overlapping segments and further comprising means for separately transmitting the results of measurements from the overlapping segments to the controller, where they are combined into a single data stream.

35. The apparatus according to claim 33, for use with overlapping segments and further comprising means for combining the results of measurements from the overlapping segments into a single data stream by the said sensor electronics, and for transmitting the single data stream to the controller.

36. The apparatus according to claim 33, for use with overlapping segments and wherein a processing means in said controller compensates for the overlapping of segments, providing a result representing the measurement of the entire line or area without gaps.

37. The apparatus according to claim 36, wherein said processing means comprises programmable logic and a related software program.

38. The apparatus according to claim 36, wherein said processing means comprises a micro-controller and a related software program.

39. The apparatus according to claim 36, wherein said processing means comprises one or a plurality of Digital Signal Processor(s) (DSP) and related software program(s).

40. A method of optimising measurement of the said spectra in real-time using the apparatus according to claim 16, wherein the relatively higher electromagnetic radiation from the zeroth order and/or from excitation (illumination) source(s) are sensed by the said photo-electric conversion device(s) and information derived immediately used to adapt for the actual location of the spectra, wherein the said zeroth order and/or excitation, as well as a plurality of spectral bandwidths are sensed via programmable two-dimensional pixel binning.

41. A method of optimising performance in real-time during measurement using the apparatus according to claim 33, wherein the measurements obtained from a single or a plurality of measurement lines is immediately evaluated by the said controller, and the result used to optimize the measurement performed by a single or a plurality of following measurement line(s).

42. A method of optimising performance in real-time during measurement from plane areas which are tilted (non-parallel) with respect to the apparatus, using the apparatus according to claim 33, wherein the position of the apparatus is adapted during the measurement such that the focus along the entire measurement line is optimal.

43. A method for optimization of sensitivity of the apparatus according to claim 33 in real time during the measurement process, whereby the location and size of the sub-areas of pixels used to measure particular wavelength bands of the spectra projected onto said photo-electric conversion device(s) are optimised by the said controller based on information previously acquired by the apparatus.

44. A method for optimization of the performance of the apparatus according to claim 33 in real time during the measurement process, whereby the spectral axis of measurement on the said photo-electric conversion device(s) is calibrated in real time using information derived from the current or previously measured spectra, wherein features in the spectra which are used for the said optimisation include the excitation (illumination) signal, reference spectral standards on the object to be measured and/or, known RAMAN scatter profiles.

45. A method of optimising performance in real-time during measurement using the apparatus according to claim 33, wherein information is acquired by the apparatus from the object to be measured, and directly used to optimize the measurements, wherein said information originates from a sample carrier, and/or from the samples themselves.

46. A method of optimising performance in real-time during measurement using the apparatus according to claim 33, wherein optical and measurement effects of mechanical tolerances, non-ideal mechanical motion are reduced or eliminated, wherein spectral effects by real-time spectral calibration, using references on the object for optimization of measurements in real-time, are corrected.

47. A method of automating the processing and/or information management of the target object(s) and/or samples to be measured using the apparatus according to claim 33, wherein information acquired by the apparatus from said object or samples to be measured serves as identification, wherein said information originates from a sample carrier, and/or from the samples themselves.

48. A method for information management of the target object(s) and/or samples to be measured using the apparatus according to claim 33, wherein the apparatus stores or writes information on the said object or samples.

49. A method for real time measurement during end-point measurement after processes and reactions using an apparatus for photo-electric measurement comprising:
   a) a single or a plurality of photo-electric conversion devices, including array sensor(s);
   b) an optical system which is modularly expandable in one axis or a plurality of axes in order to acquire electromagnetic radiation from a line or area of any desired size on an object, with any desired resolution, wherein the said optical system separates the said electromagnetic radiation modularly into a plurality of smaller segments, and projects electromagnetic radiation corresponding to the said smaller segments onto said single or a plurality of individual photo-electric conversion devices wherein said smaller segments of electromagnetic radiation originate from adjacent regions of the line or area on the object, said adjacent regions partially overlapping such that contiguity is achieved; and
   c) sensor electronics related to said photo-electric conversion device(s) which enable the operating mode and functionality of said photo-electric conversion device(s) to be defined and changed in real-time, whereby functions including the readout sequence of pixels and unlimited flexibility of pixel binning in two dimensions are fully programmable, and said photo-electric conversion devices operate and/or are controlled independently and/or simultaneously;
   measuring in real-time during a process or at an end-point after a process, reactions including those related to chemistry, bio-chemistry, biotechnology, molecular biology.

50. The method for real time measurement during end-point measurement after processes and reactions of claim 49 wherein the type of measurement comprises at least one of fluorescence, laser induced fluorescence, luminescence/chemi-luminescence, fluorescence and luminescence lifetime, reflectance and absorbance.

51. The method for real time measurement during end-point measurement after processes and reactions according to claim 49 wherein the reaction is located on microplates, micro-arrays, biological chips "biochips", samples spotted onto microscope slides, a plurality of micro-beads.

52. The method for real time measurement during end-point measurement after processes and reactions according to claim 49 wherein the reaction involves Polymerase Chain Reaction (PCR).

* * * * *